United States Patent
Babini et al.

(10) Patent No.: US 9,943,355 B2
(45) Date of Patent: Apr. 17, 2018

(54) SMOKE EVACUATION SYSTEM FOR INVASIVE SURGICAL PROCEDURES

(71) Applicant: Surgiquest, Inc., Milford, CT (US)

(72) Inventors: Carlos Babini, Easton, CT (US); Dominick Mastri, Bridgeport, CT (US); Kenneth Blier, Cheshire, CT (US); Gregory Runner, Norwalk, CT (US)

(73) Assignee: Surgiquest, Inc., Milford, CT (US)

( * ) Notice: Subject to any disclaimer, the term of this patent is extended or adjusted under 35 U.S.C. 154(b) by 80 days.

(21) Appl. No.: 15/084,740

(22) Filed: Mar. 30, 2016

(65) Prior Publication Data
US 2017/0281255 A1 Oct. 5, 2017

(51) Int. Cl.
*A61B 18/00* (2006.01)
*B01D 46/10* (2006.01)
*A61B 18/04* (2006.01)
*B01D 46/00* (2006.01)
*B01D 46/52* (2006.01)

(52) U.S. Cl.
CPC .......... *A61B 18/04* (2013.01); *B01D 46/0041* (2013.01); *B01D 46/521* (2013.01); *A61B 2218/008* (2013.01); *B01D 2279/35* (2013.01)

(58) Field of Classification Search
CPC .............. A61B 18/00; A61B 2218/008; B01D 46/0012; B01D 46/10; B01D 2253/102; B01D 2275/10; B01D 46/0038; B01S 46/0038
USPC ......... 55/385.1, 486, 503, 505, 472; 95/273, 95/286; 604/35, 45, 264
See application file for complete search history.

(56) References Cited

U.S. PATENT DOCUMENTS

| | | | | |
|---|---|---|---|---|
| 3,629,999 A | * | 12/1971 | Marsh | F24F 3/1603 454/187 |
| 3,820,536 A | * | 6/1974 | Anspach, Jr. et al. | A61G 13/108 128/202.13 |
| 4,045,192 A | * | 8/1977 | Eckstein | A61G 10/02 261/104 |
| 4,963,134 A | | 10/1990 | Backscheider et al. | |
| 5,279,599 A | | 1/1994 | Wilk | |

(Continued)

FOREIGN PATENT DOCUMENTS

DE 202015103912 U1 9/2015
GB 2309762 A1 8/1997

OTHER PUBLICATIONS

International Search Report dated Jun. 16, 2017 in connection with PCT/US2017/024879.

(Continued)

*Primary Examiner* — Frank Lawrence, Jr.
*Assistant Examiner* — Minh-Chau Pham
(74) *Attorney, Agent, or Firm* — Locke Lord LLP; Scott D. Wofsy (57) ABSTRACT

A smoke evacuation system for an open surgical site is disclosed which includes a filter cartridge assembly including a housing having an inlet port, a flow path extending from the inlet port, and a filter element disposed within the flow path, a flexible conduit having a proximal end connected to the inlet port of the filter assembly, and a smoke evacuator configured for detachable connection to a distal end of the flexible conduit for drawing smoke away from the surgical site and into the filter assembly through the conduit.

20 Claims, 6 Drawing Sheets

(56) References Cited

U.S. PATENT DOCUMENTS

| | | | |
|---|---|---|---|
| 5,522,808 A | 6/1996 | Skalla | |
| 5,941,873 A | 8/1999 | Korenfeld | |
| 6,110,259 A * | 8/2000 | Schultz | A61B 18/00 |
| | | | 55/385.1 |
| 6,524,307 B1 | 2/2003 | Palmerton et al. | |
| 6,585,791 B1 * | 7/2003 | Garito | B01D 46/0038 |
| | | | 55/385.1 |
| 6,589,316 B1 | 7/2003 | Schultz et al. | |
| 7,597,731 B2 | 10/2009 | Palmerton et al. | |
| 8,974,569 B2 | 3/2015 | Matula et al. | |
| 9,199,047 B2 | 12/2015 | Stearns et al. | |
| 9,415,160 B2 * | 8/2016 | Bonano | A61M 5/165 |
| 2014/0171855 A1 | 6/2014 | Mastri et al. | |

OTHER PUBLICATIONS

Written Opinion dated Jun. 16, 2017 in connection with PCT/US2017/024879.

* cited by examiner

SMOKE EVACUATION SYSTEM FOR INVASIVE SURGICAL PROCEDURES

BACKGROUND OF THE INVENTION

1. Field of the Invention

The subject invention is directed to surgery, and more particularly, to a smoke evacuation system for use during invasive or open surgical procedures, which includes a disposable filtration cartridge.

2. Description of Related Art

Surgical smoke and aerosol, or plume, is created when energy is imparted to tissue cells during surgery. For example, when laser or electrosurgical energy is delivered to a cell, heat is created. The heat vaporizes the intracellular fluid, which increases the pressure inside the cell and eventually causes the cell membrane to burst. When this happens, a plume of smoke containing mostly water vapor is released into the atmosphere of the operating room or doctor's office. At the same time, the intense heat created chars the protein and other organic matter within the cell, and causes thermal necrosis in adjacent cells. The charring of cells releases other harmful contaminants, such as carbonized cell fragments and gaseous hydrocarbons.

These small particles and gases are potentially hazardous if inhaled. If they are not evacuated, they become airborne and can be inhaled. This has led to the development and implementation of smoke evacuation systems during surgical procedures. A smoke evacuator is basically a vacuum pump with one or more filters designed to evacuate surgical smoke and aerosol from the operative site, filter out essentially all of the contaminants, and return the filtered air to the operating room. Different types of filters may be employed in hospital-grade smoke evacuators, including High Efficiency Particulate Air (HEPA) filter, Ultra Low Penetration Air (ULPA) filters, and activated charcoal filters.

Research confirms the effectiveness of these filter media in screening out harmful contaminants. To extend their use, filters may be impregnated with an antimicrobial agent, to inhibit the growth and reproduction of microorganisms that become trapped in the filter. The prior art also teaches that a suction canister may be installed upstream of the filter to receive any liquids suctioned during a procedure.

SUMMARY OF THE INVENTION

The subject invention is directed to a new and useful smoke evacuation system for use during an invasive or open surgical procedure. The system includes a disposable filter assembly or cartridge having a housing with an inlet port. A flow path is formed within the housing and it extends from the inlet port. A pleated filter element is disposed within the flow path for filtering smoke filled air flowing therethrough. A flexible conduit is connected to the inlet port of the filter assembly, and a smoke evacuator is connected to the flexible conduit for drawing smoke away from the surgical site and into the filter assembly through the conduit.

Preferably, the smoke evacuator includes a configurable smoke evacuation tube having a plurality of spaced apart smoke intake ports on a peripheral surface thereof. A slotted intake nozzle may be operatively associated with each smoke intake port to increase capacity. In one embodiment of the subject invention, the smoke evacuation tube has one open end and one closed end, wherein the open end is detachably coupled to the flexible conduit. In another embodiment of the subject invention, the arcuate smoke evacuation tube is closed at both ends and a branching tube extends from a central section of the smoke evacuation tube for detachably coupling with the flexible conduit.

In yet another embodiment of the subject invention, the smoke evacuator includes a corrugated tube having a suction nozzle operatively associated with a distal end thereof and a rotatable coupling is operatively associated with a proximal end thereof for detachable connection with a fitting on the distal end of the flexible conduit. The suction nozzle may be defined by an elongated intake tube, which can include an outwardly flared intake port or a bowed intake flange having a plurality of intake ports formed therein.

These and other features of the smoke evacuation system of the subject invention and the manner in which it is manufactured and employed will become more readily apparent to those having ordinary skill in the art from the following enabling description of the preferred embodiments of the subject invention taken in conjunction with the several drawings described below.

BRIEF DESCRIPTION OF THE DRAWINGS

So that those skilled in the art to which the subject invention appertains will readily understand how to make and use the smoke evacuation system of the subject invention without undue experimentation, preferred embodiments thereof will be described in detail herein below with reference to certain figures, wherein.

DETAILED DESCRIPTION OF PREFERRED EMBODIMENTS

Figure 1:
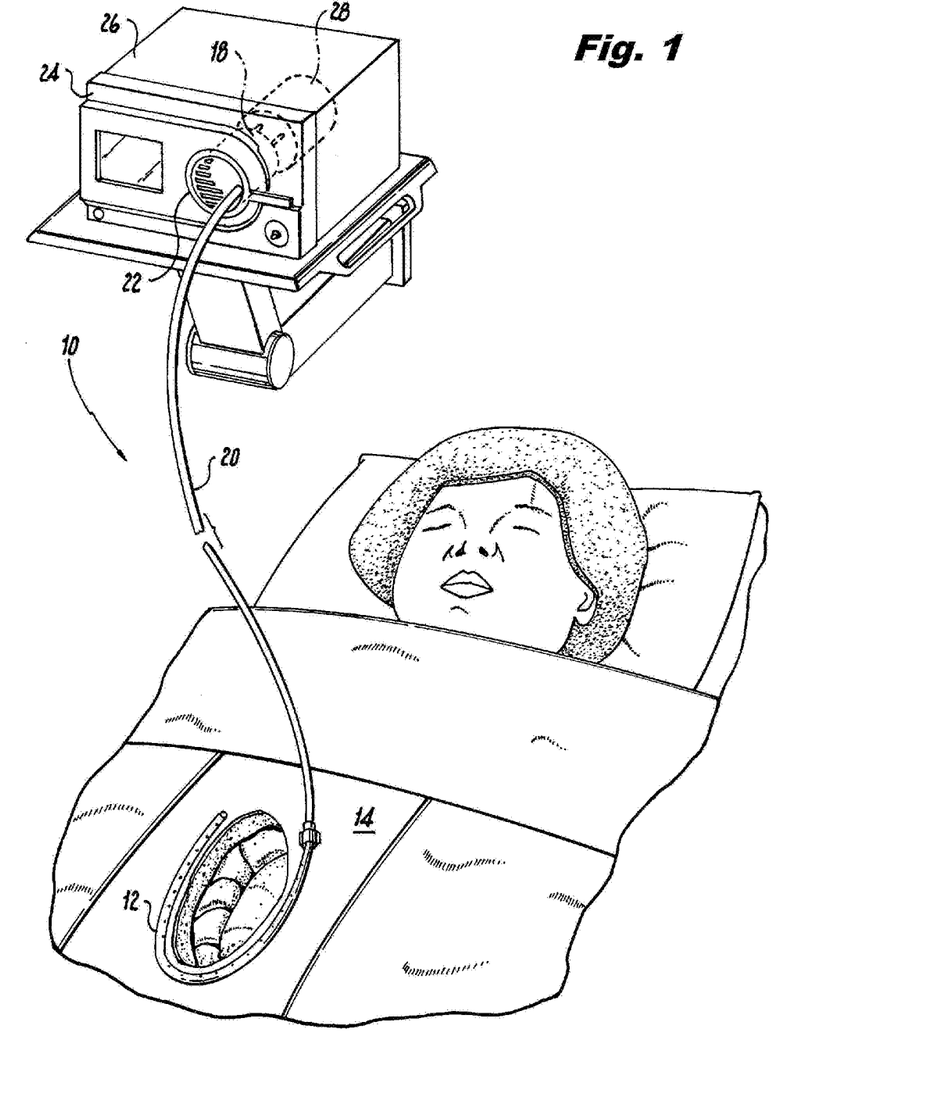
FIG. 1 is an illustration of an invasive surgical procedure involving the smoke evacuation system of the subject invention, wherein an incision in a patient is at least partially surrounded by an arcuate smoke evacuation tube connected to a filter cartridge through a flexible conduit, and wherein the filter cartridge is operatively associated with a vacuum pump located inside a device housing.

Referring now to the drawings wherein like reference numerals identify similar structural features and/or elements of the subject matter disclosed herein, there is illustrated in FIG. 1 a smoke evacuation system constructed in accordance with a preferred embodiment of the subject invention and designated generally by reference numeral 10. The smoke evacuation system 10 is adapted and configured for use during an invasive or open surgical procedure to evacuate surgical smoke from the operative site, filter out essentially all of the contaminants in the smoke, and return the filtered air to the operating room.

Figure 1A:
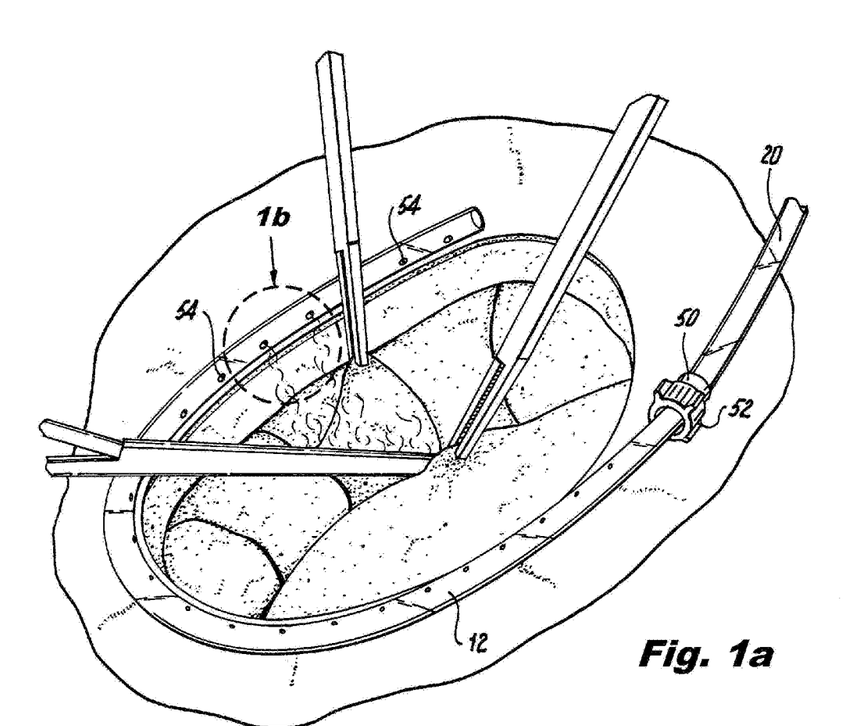
FIG. 1a is an enlarged view of the open incision in the patient's abdominal cavity during a surgical procedure in which smoke is being generated and evacuated through the system of the subject invention.

Referring to FIG. 1, the smoke evacuation system 10 includes a flexible or otherwise configurable smoke evacuation tube 12 that is dimensioned and configured to at least partially surround an open incision in the abdominal wall of a patient. For example, the configurable smoke evacuation tube 12 can be arranged in a curved or arcuate configuration relative to the open incision, as illustrated in FIG. 1a.

Figures 2, 2A:
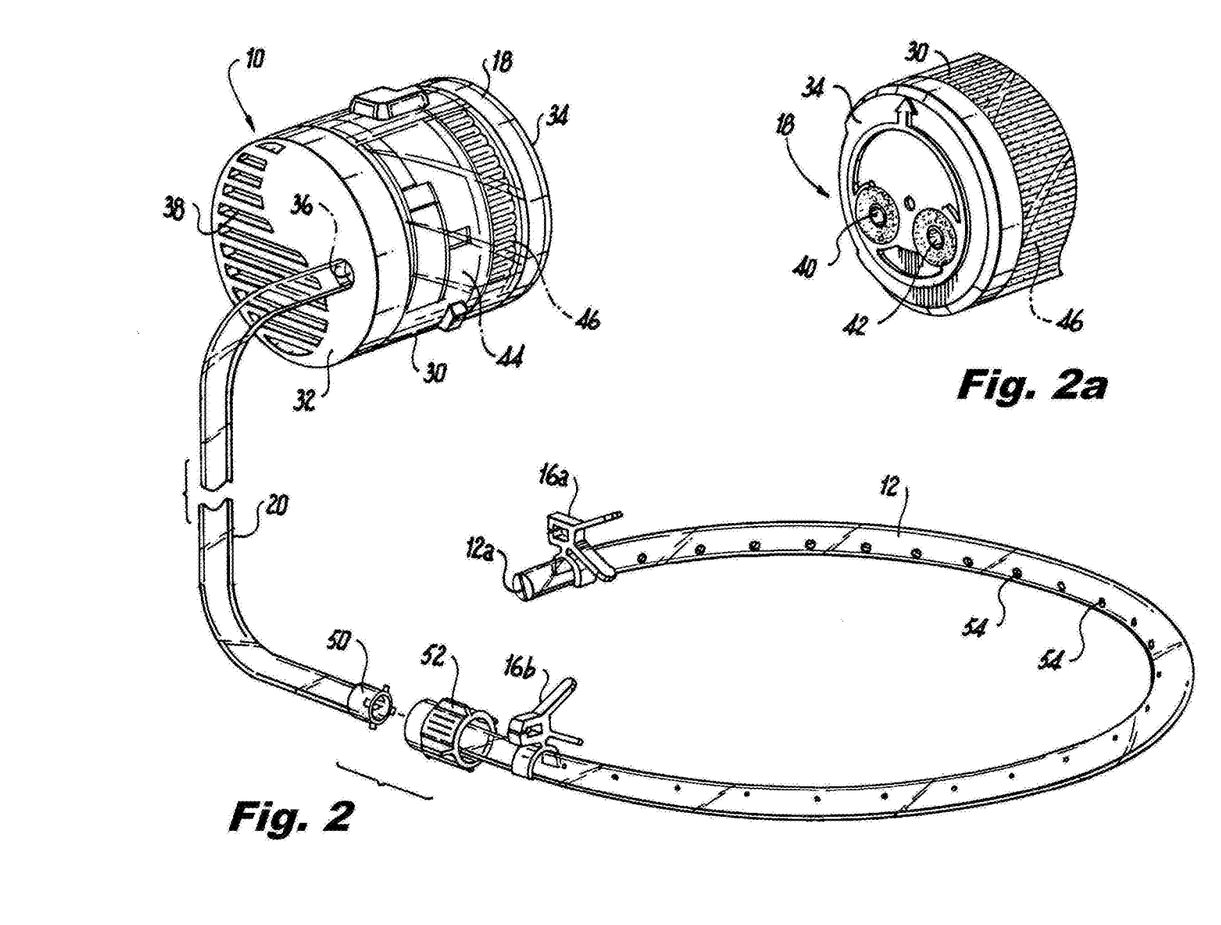
FIG. 2 is an enlarged perspective view of the smoke evacuation system shown in FIG. 1 separate from the vacuum pump, wherein the arcuate smoke evacuation tube includes a plurality of spaced apart smoke intake ports on a radially inner peripheral surface thereof.

The smoke evacuation tube 12 may be readily secured to the surgical drape 14 covering the patient by a plurality of clamps 16 (see FIG. 2). The proximal end of the smoke evacuation tube 12 it is connected to a disposable filter cartridge assembly 18 by way of a flexible conduit 20. Those skilled in the art will readily appreciate that the diameter and length of the smoke evacuation tube 12 can vary depending upon the application, patient or surgical procedure with which it is employed. Similarly, the length of the flexible conduit 20 can vary depending upon the application and other physical parameters associated with the operating room.

The filter cartridge 18 is operatively associated with or otherwise releasably engaged within a reception port 22 in the front panel 24 of a surgical gas delivery device housing 26 that contains a vacuum pump 28 for drawing smoke into the smoke evacuation system 10. An example of such a gas delivery device with a vacuum pump is disclosed in commonly assigned U.S. Pat. No. 9,199,047 to Stearns et al., the disclosure of which his incorporated herein by reference in its entirety.

Referring now to FIG. 2, the filter cartridge 18 has a generally cylindrical plastic housing 30 with a front end cap 32 and a rear end cap 34. The front end cap 32 includes inlet port 36 for connecting with a proximal end of the flexible conduit 20. The front end cap 32 also includes outlet vent slots 38 opening to atmosphere for permitting filtered air to return back into the operating room. The rear end cap 34 includes a sealed rear outlet port 40 for communicating with an inlet side of the vacuum pump 28 and a sealed rear inlet port 42 for communicating with an outlet side of the vacuum pump 28, as shown in FIG. 2a.

Moreover, the rear outlet port 40 in rear end cap 34 communicates with the inlet port 36 in the front end cap 32, while the rear inlet port 42 in rear end cap 34 communicates with the outlet vent slots 38 in the front end cap 32. That is, an internal flow path 44 is formed within the housing 30 of filter cartridge 18 and it extends between the front inlet port 36 in front end cap 32 and the rear outlet port 40 in the rear end cap 34 to channel smoke filled air drawn into the filter 18 by the vacuum pump 28. A pleated filter element 46 is disposed within the flow path 44 for filtering smoke drawn into the filter cartridge 18 by the vacuum pump 28. The media of filter element 46 can take the form of a High Efficiency Particulate Air (HEPA) filter, an Ultra-Low Penetration Air (ULPA) filter, or the like.

It is envisioned that a second filter element (not shown) can be disposed within the housing 30 of filter cartridge 18 for filter air entering the filter cartridge 18 from the outlet side of the vacuum pump 28 before it is delivered back into the operating room through the outlet vent slots 38 in the front end cap 32. It is also envisioned that an internal reservoir (not shown) can be formed within the housing 30 of filter cartridge 18, in line with the filter element 46, to accommodate the accumulation of fluids drawn into the cartridge by the vacuum pump 28.

The distal end of the flexible conduit 20 extending from the inlet port 36 in the front end cap 32 of the housing 30 of filter cartridge 18 includes a mechanical fitting 50 for rotational engagement with a corresponding rotatable coupling 52 located on the proximal end of the smoke evacuation tube 12. A rotational coupling arrangement of this type is disclosed, for example, in commonly assigned U.S. Patent Application Publication 2014/0171855 to Mastri et al., the disclosure of which is incorporated herein by reference in its entirety. The distal end 12a of the configurable smoke evacuation tube 12, opposite the coupling 52, is plugged or otherwise closed.

Figure 1B:
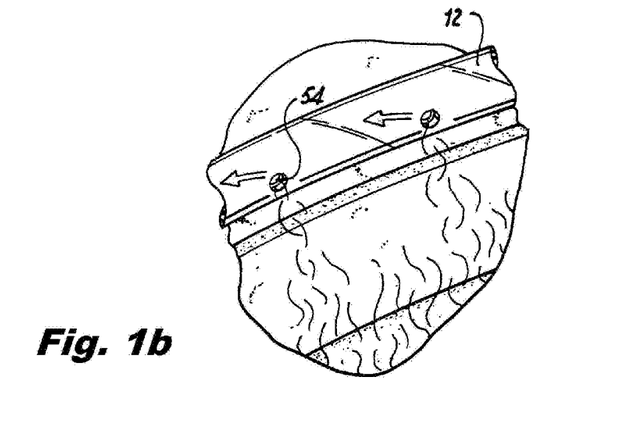
FIG. 1b is an enlarged localized view of the smoke evacuation tube of the subject invention as smoke is drawing into the intake ports formed on the radially inner peripheral surface thereof.

The smoke evacuation tube 12 has a plurality of spaced apart smoke intake ports 54 located on a radially inner peripheral surface thereof for admitting smoke generated during a surgical procedure into the central lumen of the smoke evacuation tube 12, as best seen in FIG. 1b. More particularly, smoke filled air is drawn into the intake ports 54 through the action of vacuum pump 28 in device housing 26. Those skilled in the art will readily appreciate that the size and spacing of the intake ports 54 can vary depending upon the application or procedure. As shown in FIG. 2, at least two clamps 16a and 16b are associated with the smoke evacuation tube 12 for securing the tube to a surgical drape or the like. More or fewer clamps could be employed.

Figure 3:
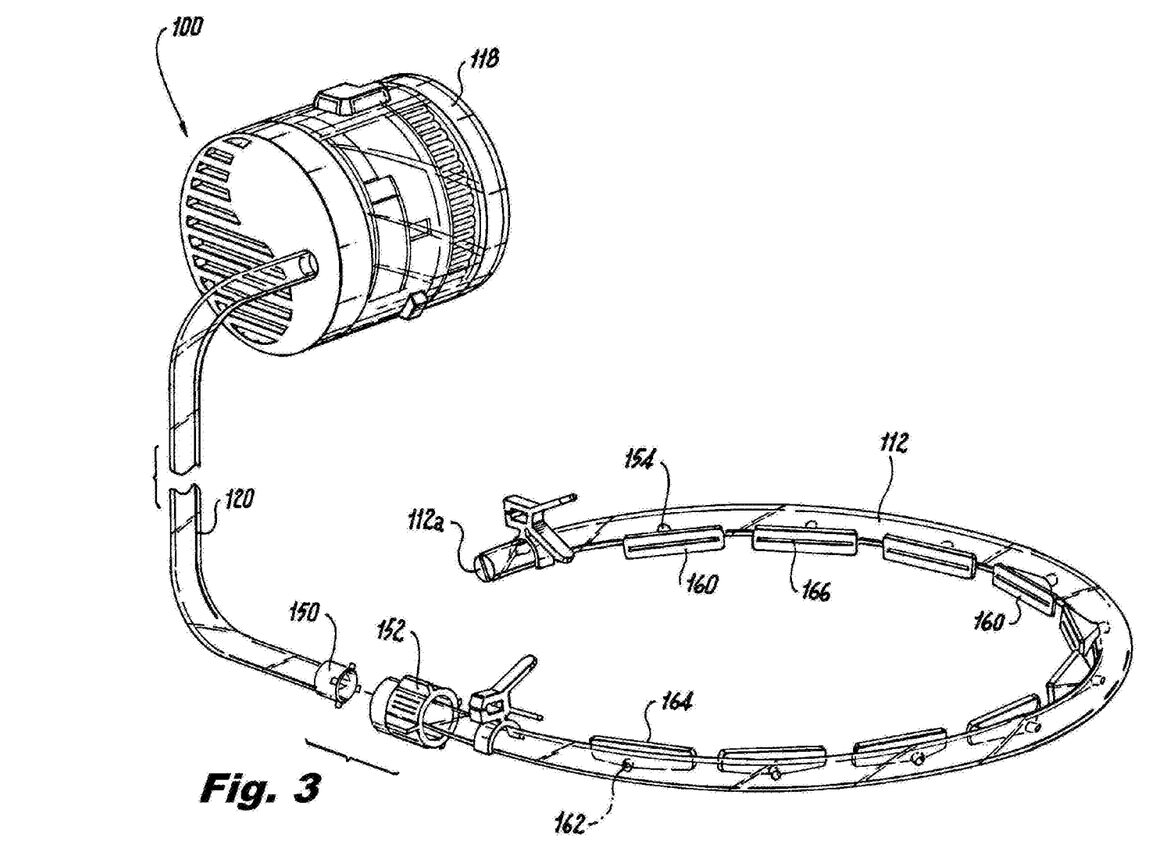
FIG. 3 is a perspective view an embodiment of the smoke evacuation system of the subject invention wherein suction nozzles are associated with each smoke intake port of the arcuate smoke evacuation tube.

Referring to FIG. 3, there is illustrated another embodiment of the smoke evacuation system of the subject invention, which is designated generally by reference numeral 100. This smoke evacuation system is substantially similar to smoke evacuation system 10 in that it includes a flexible and configurable smoke evacuation tube 112 with a closed distal end 112a and a coupling 152 at its proximal end, a disposable filter cartridge 118, and a flexible conduit 120 with a mechanical fitting 150 extending between the smoke evacuation tube 112 and the filter cartridge 118.

Smoke evacuation system 100 differs from smoke evacuation system 10 in that a slotted intake nozzle 160 is operatively associated with each smoke intake port 154 formed in the periphery of smoke evacuation tube 112. More particularly, each slotted nozzle 160 include a central stem 162 which is engaged in a corresponding intake port 154 and a generally rectangular body portion 164 that has an elongated smoke intake slot 166. The smoke intake slots 166 advantageously increase the overall smoke evacuation capacity of the system 100 relative to system 10.

Figure 4:
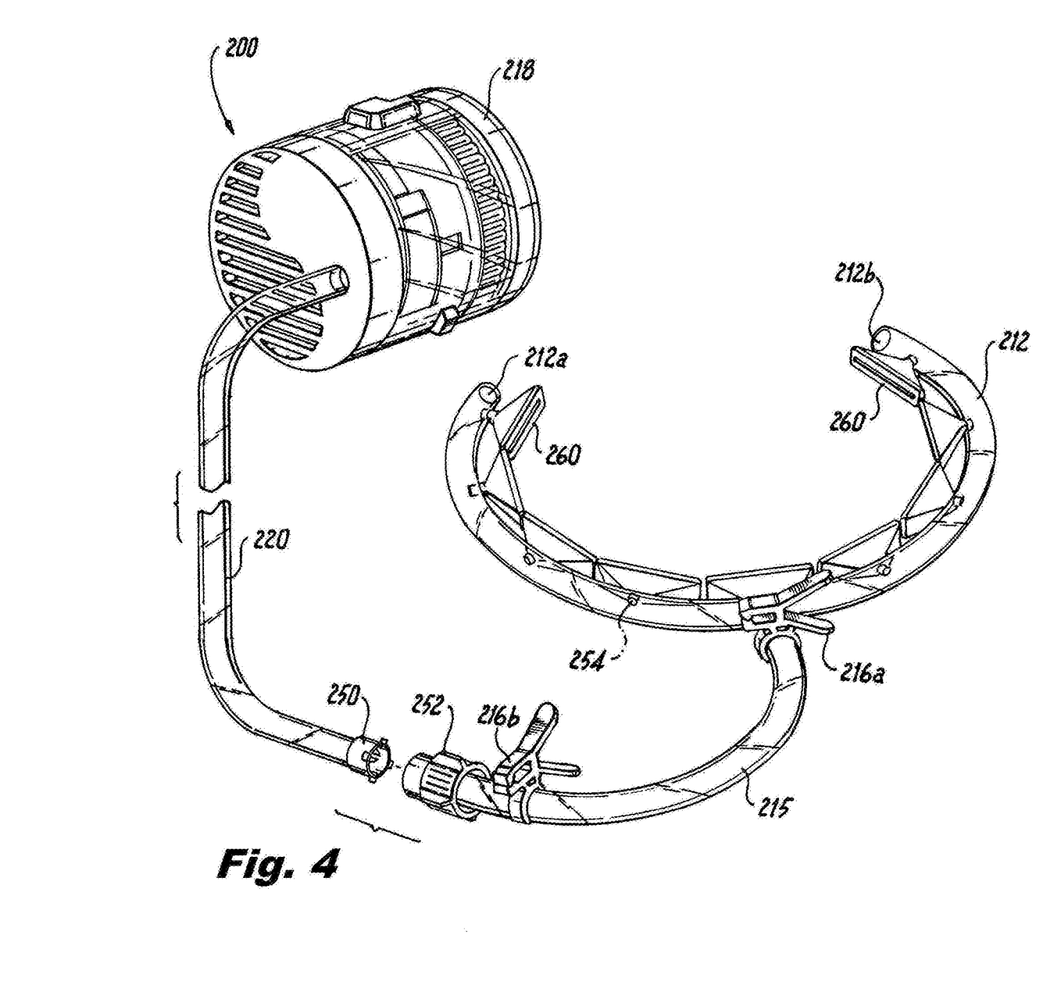
FIG. 4 is a perspective view of another embodiment of the smoke evacuation system of the subject invention wherein the arcuate smoke evacuation tube includes a branching tube for coupling to the flexible conduit.

Referring now to FIG. 4, there is illustrated another embodiment of the smoke evacuation system of the subject invention, which is designated generally by reference numeral 200. This system is substantially similar to smoke evacuation system 100 in that it includes a configurable smoke evacuation tube 212, a disposable filter cartridge 218 and a flexible conduit 220 extending between the smoke evacuation tube 212 and the filter cartridge 218. The smoke evacuation tube 212 also includes slotted intake nozzles 260 operatively associated with each smoke intake port 254.

Smoke evacuation system 200 differs from smoke evacuation system 100 in that the smoke evacuation tube 212 is closed or otherwise plugged at both of its ends 212a, 212b, and a branching tube 215 extends from a central section of the smoke evacuation tube 212 to detachably connect with the flexible conduit 220 extending to the filter cartridge 218. More particularly, the proximal end of the branching tube 215 includes a rotational coupling 252 for connection with the fitting 250 on the distal end of flexible conduit 220. In this embodiment, clamps 216*a* and 216*b* are associated with the branching tube 215, and others may be associated with the smoke evacuation tube 212, although not shown.

Figure 5:
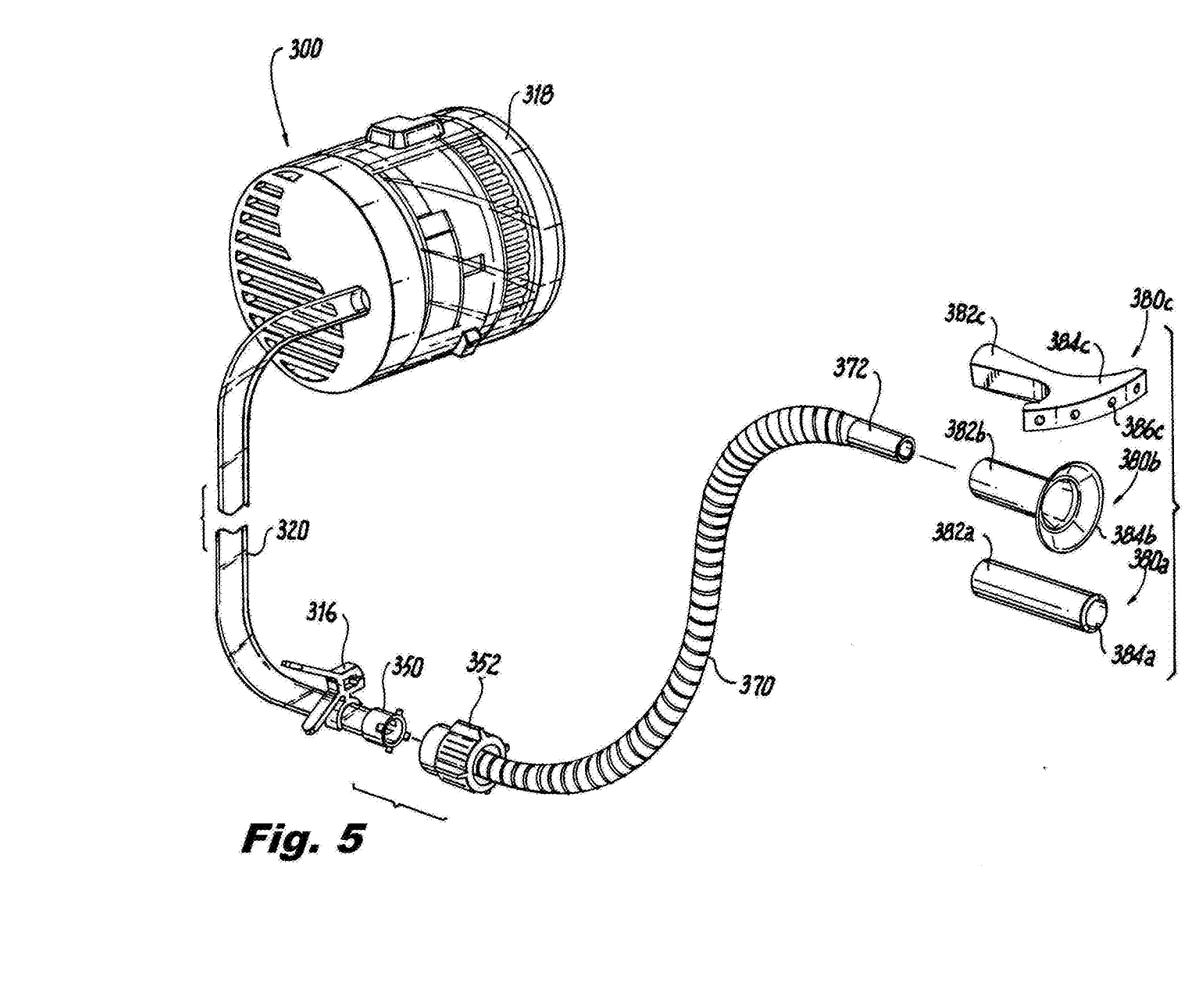
FIG. 5 is a perspective view of yet another embodiment of the smoke evacuation system of the subject invention wherein the smoke evacuation system includes a corrugated tube having a suction nozzle at a distal end thereof.

Referring to FIG. 5, there is illustrated yet another embodiment of the subject invention, which is designated generally by reference numeral 300. This embodiment is similar to the previously disclosed embodiments of the subject invention in that it includes a disposable cartridge 318 connected to a flexible conduit 320 that has a mechanical fitting 350 at a distal end thereof for connection with a rotational coupling 352. However, in this embodiment, a corrugated smoke evacuation tube 370 extends from the coupling 352.

The corrugated smoke evacuation tube 370 has an open tapered distal end section 372 for receiving a suction nozzle 380*a*-380*c*. More particularly, suction nozzle 380*a* is defined by an elongated cylindrical intake tube 382*a* having an inlet port 384*a*, suction nozzle 380*b* is defined by an elongated intake tube 382*b* having an outwardly flared intake port 384*b*, and suction nozzle 380*c* is defined by an elongated intake tube 382*c* having a bowed intake flange 384*c* having a plurality of intake ports 386*c* formed therein.

In this embodiment of the invention, a drape clip 316 can be associated with the flexible conduit 320, adjacent the fitting 352. During a procedure, a surgeon or surgical assistant can select one and attach one of the suction nozzles 380*a*-380*c* to the distal section 372 of the tube 370 and dynamically position that suction nozzle in or near the incision, to provide a more direct means of smoke evacuation than the previously disclosed embodiments of the subject invention, wherein the smoke evacuation tubes are typically arranged in a more stationary position relative to the incision.

While the smoke evacuation system of the subject invention has been shown and described with reference to several preferred embodiments, those skilled in the art will readily appreciate that various changes and/or modifications may be made thereto without departing from the spirit and scope of the subject invention as defined by the appended claims.

What is claimed is:

1. A smoke evacuation system for an open surgical site, comprising:
   a) a filter assembly including a housing having a front end cap and a rear end cap, the front end cap having a front inlet port and front outlet vent slots opening to atmosphere, the rear end cap having a sealed rear inlet port and a sealed rear outlet port, the filter assembly further including an internal inlet flow path providing communication between the front inlet port of the front end cap and the rear outlet port of the rear end cap, and an internal outlet flow path providing communication between the rear outlet port of the rear end cap and the front outlet vent slots of the front end cap, and a filter element disposed within the internal inlet flow path for filtering air drawn into the filter assembly from the surgical site;
   b) a flexible conduit having a proximal end connected to the front inlet port of the filter assembly; and
   c) a smoke evacuator configured for detachable connection to a distal end of the flexible conduit for drawing smoke filled air away from the surgical site and into the filter assembly through the flexible conduit.

2. A smoke evacuation system as recited in claim 1, wherein the distal end of the flexible conduit includes a mechanical fitting for connecting with a coupling associated with the smoke evacuator.

3. A smoke evacuation system as recited in claim 2, wherein the smoke evacuator includes a configurable smoke evacuation tube having a plurality of spaced apart smoke intake ports on a peripheral surface thereof.

4. A smoke evacuation system as recited in claim 3, wherein the smoke evacuation tube is closed at both ends.

5. A smoke evacuation system as recited in claim 3, wherein the smoke evacuation tube has an open end and a closed end.

6. A smoke evacuation system as recited in claim 3, wherein a slotted intake nozzle is operatively associated with each smoke intake port.

7. A smoke evacuation system as recited in claim 4, wherein a branching tube extends from the smoke evacuation tube to the flexible conduit.

8. A smoke evacuation system as recited in claim 1, wherein at least one drape clip is operatively associated with the smoke evacuator.

9. A smoke evacuation system as recited in claim 5, wherein a rotatable coupling is operatively associated with the open end of the smoke evacuation tube for connection with the fitting on the distal end of the flexible conduit.

10. A smoke evacuation system as recited in claim 7, wherein a rotatable coupling is operatively associated with an open end of the branching tube for connection with the fitting on the distal end of the flexible conduit.

11. A smoke evacuation system as recited in claim 2, wherein the smoke evacuator includes a corrugated tube having a suction nozzle operatively associated with a distal end thereof and a rotatable coupling operatively associated with a proximal end thereof for connection with the fitting on the distal end of the flexible conduit.

12. A smoke evacuation system as recited in claim 11, wherein the suction nozzle is defined by an elongated intake tube.

13. A smoke evacuation system as recited in claim 12, wherein the intake tube includes an outwardly flared intake port.

14. A smoke evacuation system as recited in claim 12, wherein the intake tube includes a bowed intake flange having a plurality of intake ports formed therein.

15. A smoke evacuation system for an open surgical site, comprising:
   a) a filter assembly including a housing having a front end cap and a rear end cap, the front end cap having a front inlet port and front outlet vent slots opening to atmosphere, the rear end cap having a sealed rear inlet port and a sealed rear outlet port, the filter assembly further including an internal inlet flow path providing communication between the front inlet port of the front end cap and the rear outlet port of the rear end cap, and an internal outlet flow path providing communication between the rear outlet port of the rear end cap and the front outlet vent slots of the front end cap, and a pleated filter element disposed within the internal inlet flow path for filtering air drawn into the filter assembly from the surgical site;
   b) a flexible conduit having a proximal end connected to the inlet port of the filter assembly and a distal end having a mechanical fitting associated therewith; and
   c) a configurable smoke evacuation tube configured for detachable connection with the fitting on the distal end of the flexible conduit and having a plurality of spaced apart smoke intake ports on a peripheral surface thereof for drawing smoke away from the surgical site and into the filter assembly through the flexible conduit.

16. A smoke evacuation system as recited in claim 15, wherein the smoke evacuation tube has an open end and a closed end.

17. A smoke evacuation system as recited in claim 15, wherein the smoke evacuation tube is closed at both ends.

18. A smoke evacuation system as recited in claim 17, wherein a branching tube extends from a central section of the smoke evacuation tube to the flexible conduit.

19. A smoke evacuation system as recited in claim 15, wherein a slotted intake nozzle is operatively associated with each smoke intake port.

20. A smoke evacuation system as recited in claim 15, wherein a rotatable coupling is operatively associated with the smoke evacuation tube for detachable connection with the fitting on the distal end of the flexible conduit.

\* \* \* \* \*

UNITED STATES PATENT AND TRADEMARK OFFICE
CERTIFICATE OF CORRECTION

PATENT NO. : 9,943,355 B2
APPLICATION NO. : 15/084740
DATED : April 17, 2018
INVENTOR(S) : Carlos Babini et al.

It is certified that error appears in the above-identified patent and that said Letters Patent is hereby corrected as shown below:

In the Claims

Column 5 Line 53 in Claim 1, should read: between the rear inlet port of the rear end cap and the
Column 6 Line 54 in Claim 15, should read: between the rear inlet port of the rear end cap and the Signed and Sealed this
Thirteenth Day of August, 2019

Andrei Iancu
*Director of the United States Patent and Trademark Office*